(12) United States Patent
Liu et al.

(10) Patent No.: US 11,567,018 B2
(45) Date of Patent: Jan. 31, 2023

(54) CEMENT PERFORMANCE EVALUATION DEVICE AND CEMENT DESIGN METHOD FOR CEMENTING IN PENETRATED HYDRATE DEPOSIT

(71) Applicant: CHINA UNIVERSITY OF PETROLEUM (EAST CHINA), Qingdao (CN)

(72) Inventors: Huajie Liu, Qingdao (CN); Yuhuan Bu, Qingdao (CN); Shenglai Guo, Qingdao (CN); Chang Lu, Qingdao (CN); Xinyang Guo, Qingdao (CN); Shengda Shen, Qingdao (CN); Rui Ma, Qingdao (CN)

(73) Assignee: CHINA UNIVERSITY OF PETROLEUM (EAST CHINA), Qingdao (CN)

( * ) Notice: Subject to any disclaimer, the term of this patent is extended or adjusted under 35 U.S.C. 154(b) by 0 days.

(21) Appl. No.: 17/580,687

(22) Filed: Jan. 21, 2022

(65) Prior Publication Data

US 2022/0236203 A1   Jul. 28, 2022

(30) Foreign Application Priority Data

Jan. 21, 2021 (CN) .......................... 202110082094.1
Jul. 1, 2021 (CN) .......................... 202110746567.3

(51) Int. Cl.
*E21B 33/14* (2006.01)
*G01N 25/18* (2006.01)
(Continued)

(52) U.S. Cl.
CPC ............. *G01N 25/18* (2013.01); *E21B 33/14* (2013.01); *E21B 49/02* (2013.01); *G01N 33/383* (2013.01)

(58) Field of Classification Search
CPC ....................................................... G01N 3/12
See application file for complete search history.

(56) References Cited

U.S. PATENT DOCUMENTS

| | | | |
|---|---|---|---|
| 2009/0084189 A1* | 4/2009 | McMechan | G01N 3/12 73/803 |
| 2014/0174732 A1* | 6/2014 | Goodwin | E21B 33/13 166/255.1 |
| 2014/0354443 A1* | 12/2014 | Roberson | E21B 47/10 340/853.2 |

OTHER PUBLICATIONS

Xu Mingbiao, et al., The Research of Low-heat Slurry for Cementing in the Natural Gas Hydrate Formation, Journal of Oil and Gas Technology, 2014, pp. 134-137, vol. 36, No. 11.
(Continued)

*Primary Examiner* — William D Hutton, Jr.
*Assistant Examiner* — Avi T Skaist
(74) *Attorney, Agent, or Firm* — Bayramoglu Law Offices LLC

(57) ABSTRACT

A performance evaluation device and a design method of a cement for well cementing in a penetrated hydrate layer are provided. The performance evaluation device includes an equivalent wellbore, an inner circulation system, an outer circulation system, a thermal insulation cover, a bracket, a temperature sensing system, and a cement mold. The device can simulate a true downhole situation, conduct an evaluation experiment on the heat insulation performance of a cementing cement, and conduct experiments at different temperatures with automatic temperature control. The design method is to use a low-hydration, early-strength, and heat-insulating cement slurry system during the well cementing in a penetrated hydrate layer, where the low-hydration and early-strength characteristics ensure the effective sealing of a hydrate layer during a cementing process, and the heat insulation characteristic results in low heat
(Continued)

conductivity and thus can ensure the stability of a hydrate layer during a production operation.

7 Claims, 6 Drawing Sheets

(51) Int. Cl.
*E21B 49/02* (2006.01)
*G01N 33/38* (2006.01)

(56) References Cited

OTHER PUBLICATIONS

Xi Fangzhu, et al., Study of deepwater low-temperature cement slurry, Oil Drilling & Production Technology, 2010, pp. 40-44, vol. 32, No. 1.

* cited by examiner

US 11,567,018 B2

CEMENT PERFORMANCE EVALUATION DEVICE AND CEMENT DESIGN METHOD FOR CEMENTING IN PENETRATED HYDRATE DEPOSIT

TECHNICAL FIELD

The present disclosure belongs to the field of oil and gas well cementing, and particularly relates to a performance evaluation device and design method of a cement for well cementing in a penetrated hydrate layer.

BACKGROUND

In recent years, some traditional blocks of onshore oil fields have faced many problems in an exploitation process, such as declining production, increasing difficulty in potential tapping, and rising exploitation cost, making deep-sea oil and gas resources gradually become a new development hotspot. As an important process linking deep-water drilling and well completion, deep-water cementing is an important guarantee for the safe, economical, and efficient exploitation of deep-water oil and gas resources. Although marine oil and gas resources are abundant, there will be gas hydrate layers in subsea shallow layers due to a low-temperature and high-pressure environment in a deep-water area. A gas hydrate layer penetrated by a casing pipe is called a penetrated hydrate layer, and a gas hydrate layer not penetrated by a casing pipe is called an independent hydrate layer (as shown in FIG. 1). A gas hydrate layer existing in a deep-water shallow layer is normally stable, but the gas hydrate will be thermally decomposed to generate a gas when heat generated by an exothermic reaction of hydration during wait-on-cement (WOC) is transferred to the hydrate layer, which results in damage and micro-gaps at a cementing interface between a cement sheath and a casing pipe, thereby causing the failure of cement seal integrity and even the occurrence of blowout and other hazards. Experts and scholars in the cementing field have paid enough attention to this issue, and have developed various low-temperature, early-strength, and low-hydration-heat cement slurry systems (Xu Mingbiao, Wang Xiaoliang, Zhou Jianliang, et al. Research on Low-Heat Cement Slurry for Cementing through Gas Hydrate Layer [J]. Journal of Oil and Gas Technology, 2014 (11): 134-137; and Xi Fangzhu, Qu Jiansheng, Lv Guangming, et al. Research on Cement Slurry for Deep-water Low-Temperature Cementing [J]. Oil Drilling & Production Technology, 2010, 32 (1): 40-44). Cement slurry systems with excellent performance solve the problem of hydrate decomposition during WOC to some extent.

However, in a process of deep oil and gas production, when the deep oil and gas flows in an oil pipe, heat carried by the oil and gas is transferred to a penetrated hydrate layer through the combination of the oil pipe and a casing pipe; once a temperature of an interface between the hydrate layer and a well-cementing cement paste exceeds a decomposition temperature of the hydrate, the hydrate layer will be decomposed, resulting in the separation of an established artificial wellbore from a formation, the failure of effective support, and the subsidence of a wellhead; the gush of natural gas resulting from the decomposition of the hydrate may cause the natural gas to escape from the surface casing pipe, and in severe cases, it may even cause blowouts, and slip and, collapse of shallow formations. At present, once encountering a shallow area with a hydrate layer, a solution to avoid the hydrate layer or induce the hydrate to flow is generally adopted, resulting in disruption of a development well pattern layout or waste of resources. At present, there are few reports on research in this aspect. Therefore, the development of a low-temperature, early-strength, and low-hydration-heat cement slurry system cannot fundamentally solve the problem that the decomposition of a hydrate layer causes the decline in cementing quality. In order to prevent the thermal decomposition of a hydrate during a production process, it is necessary to improve the thermal insulation capacity of a cement sheath near the hydrate layer, such that a solidified cement sheath can well block heat in an annulus in a wellbore and prevent the heat in the wellbore from spreading to a formation. Therefore, it is necessary to study the thermal insulation performance of cement.

SUMMARY

The present disclosure is intended to provide a performance evaluation device and design method of a cement for well cementing in a penetrated hydrate layer.

The performance evaluation device of a cement for well cementing in a penetrated hydrate layer includes:

an outer cavity body with a cavity inside, where a partition is arranged inside the outer cavity body, and the partition divides the cavity inside the outer cavity body into two independent spaces, namely, an outer circulation cavity and a placement cavity; and a thermal insulation layer is arranged on an outer wall of the outer cavity body;

an equivalent wellbore arranged in the placement cavity, where a through-cavity that penetrates up and down is formed inside the equivalent wellbore; the equivalent wellbore has a double-walled structure, and an annular cavity is formed between two walls; and a liquid inlet and a liquid outlet that communicate with the annular cavity are formed at two ends of the equivalent wellbore, respectively;

an inner cavity body inserted into the through-cavity, where an inner circulation cavity is formed inside the inner cavity body; and a capped edge is arranged at a top of the inner cavity body, and the capped edge is clamped at the top of the inner cavity body;

a thermal insulation cover pressed against the outer cavity body and a top of the equivalent wellbore;

an outer circulation system including a low-temperature thermostatic bath, where the low-temperature thermostatic bath communicates with the outer circulation cavity through an outer circulation pipeline to form the outer circulation system;

an inner circulation system including a high-temperature thermostatic bath, where the high-temperature thermostatic bath communicates with the inner circulation cavity through an inner circulation pipeline to form the inner circulation system; and a temperature sensing system, where the temperature sensing system includes a group A of temperature sensors, a group B of temperature sensors, and a temperature measuring instrument, and the group A of temperature sensors and the group B of temperature sensors are arranged in the placement cavity and are each electrically connected to the temperature measuring instrument.

Preferably, a stepped hole communicating with the outside may be formed at a bottom of the outer cavity body, and the equivalent wellbore may be fitted in the stepped hole.

Preferably, a countersunk head screw may be threadedly connected in the liquid inlet and the liquid outlet.

Preferably, a central hole may be formed on the thermal insulation cover, and the capped edge may be inserted into the central hole.

Preferably, the performance evaluation device may further include a cement mold for assisting in the filling of sand and mud.

Preferably, the performance evaluation device may further include a compactor for compacting the sand and mud.

In the present disclosure, the performance may refer to physicochemical thermal performance of the cement, including but not limited to cement hydration exothermic performance, cement paste strength performance, and cement paste thermal conductivity.

Since gas hydrates widely exist in deep-water shallow formations, a borehole trajectory easily penetrates through a hydrate layer during an on-site drilling operation, and in this case, the hydration heat release during WOC and the heat transfer in an oil pipe during subsequent production operations will both cause hydrate instability and decomposition. Therefore, the present disclosure expands a theory to solve the deep-water cementing of such a hydrate layer, and uses a low-hydration, early-strength, and heat-insulating cement slurry system during the well cementing, where the ow-hydration and early-strength characteristics ensure the effective sealing of a hydrate layer during a cementing process, and the heat insulation characteristic results in low heat conductivity and thus can ensure the stability of a hydrate layer during a production operation, which fundamentally solves the cementing quality problem of a hydrate layer.

The design method of a cement for well cementing in a penetrated hydrate layer according to the present disclosure includes the following steps:

(1) collecting a formation sample of a cementing-target penetrated hydrate layer, testing physical parameters of the formation, and acquiring environmental parameters of the cementing-target layer;

(2) analyzing the obtained physical parameters of the formation, and determining early, strength performance requirements, hydration heat performance requirements, and heat insulation performance requirements of a cement slurry that meets cementing conditions based on field operation requirements;

(3) according to the early strength performance requirements of the cement slurry, testing effects of various early-strength agents, and selecting an early-strength agent with the optimal performance;

(4) according to the hydration heat performance requirements of the cement slurry, testing effects of various low-hydration-heat materials, and selecting a low-hydration-heat material with the optimal performance;

(5) according to the heat insulation performance requirements of the cement slurry, testing effects of various heat-insulating materials, and selecting a heat-insulating material with the optimal performance, where the heat-insulating material includes, but is not limited to, a hollow glass microsphere MGM), obturator perlite, or a vitrified micro bubble (VMB);

(6) preparing the selected early-strength agent, low-hydration-heat material, and heat-insulating material and the cement slurry into the low-hydration, early-strength, and heat-insulating cement slurry system to adjust the performance of the cement slurry, such that the cement slurry has low hydration, early strength, and heat insulation performance and meets the requirements of cementing construction;

(7) using a performance evaluation device of a cement for well cementing in a penetrated hydrate layer to simulate a cementing process of the penetrated hydrate layer, and determining whether the performance of the low-hydration, early-strength, and heat-insulating cement slurry system meets the requirements; and if the requirements are met, proceeding to step (8), and if the requirements are not met, repeating steps (3) to (6); and (8) estimating a cement slurry injection volume required by the target layer, and injecting a low-hydration, early-strength, and heat-insulating cement slurry meeting test requirements into the formation in the form of a displacement liquid according to field operation conditions and corresponding construction parameters until the cement slurry reaches a predetermined solidification range.

Further, the physical parameters of the formation may include, but are not limited to, formation temperature, formation pressure, and hydrate saturation.

Further, the cement slurry should have a consistency of less than 70 Bearden before being completely pumped into the formation, such that the slurry will remain in a flowable state during a construction process, which facilitates the penetration of the slurry; when the cement slurry is pumped, a pumping pressure should be reasonably controlled to avoid a large amount of cement slurry loss caused by the pressure leakage formation as much as possible; and the pumping time of the cement slurry should be controlled within 1 hour to 2 hours, and a long time will cause a high economic cost. A compressive strength of the cement slurry should be no less than 3.5 NIPa within 24 hours at 20° C., such that the formed cement sheath exhibits a supporting effect.

Further, the simulation experiment device for cementing through a penetrated hydrate layer should include a temperature control module, a pressure control module, a formation simulation module, a cement slurry pumping module, a production simulation module, and a stability detection module, and the device can simulate the entire process of cement slurry pumping and solidification in a hydrate formation environment.

The determining whether the performance of the low-hydration, early-strength, and heat-insulating cement slurry system meets the requirements in step (7) may include the following specific steps:

S1: placing an equivalent wellbore into a placement cavity inside an outer cavity body, and adding an equivalent fluid to an annular cavity of the equivalent wellbore;

S2: hoisting an inner cavity body into a through-cavity of the equivalent wellbore, and lowering until a capped edge at an upper end of the inner cavity body is clamped at an upper end of the equivalent wellbore; and allowing a high-temperature thermostatic bath to communicate with an inner circulation cavity through an inner circulation pipeline to form an inner circulation system;

S3: adding sand and mud into the placement cavity inside the outer cavity body to form an annular sand and mud layer, compacting the sand and mud layer, and reserving an annular space between the sand and mud layer and an outer wall of the equivalent wellbore;

S4: slowly pouring the prepared cement slurry into the annular space between the sand and mud layer and the outer wall of the equivalent wellbore; and when the cement is slightly solidified, inserting metal shells of the group A of temperature sensors into the cement at equal intervals in a radial direction, and inserting metal shells of the group B of temperature sensors into the sand and mud at equal intervals in the radial direction, where the metal shells are inserted at a depth that makes a bottom end of the metal shell in the middle of the cement or the sand and mud;

S5: after the cement is completely solidified, inserting probes of the group A and group B of temperature sensors into the metal shells sequentially, and connecting the probes to the temperature measuring instrument;

S6: allowing a low-temperature thermostatic bath to communicate with an outer circulation cavity through an outer circulation pipeline to form an outer circulation system, opening the low-temperature thermostatic bath and covering a thermal insulation cover to cool the entire device, and starting the experiment after a temperature is stable;

S7: opening the high-temperature thermostatic bath to heat the inner cavity body, recording a temperature change curve of each temperature sensor, and closing the high-temperature thermostatic bath and the low-temperature thermostatic bath when a temperature remains unchanged; and S8: comparing an experimental result with a performance index, and determining a heat insulation performance rate of the cement slurry used in the experiment to evaluate the performance of the cement.

Preferably, a preparation method of the cement slurry in S4 may include: according to a required cement sheath cementing experiment, weighing various solid materials by an electronic scale based on a cement slurry formula given on site, pouring the solid materials into a bucket, and thoroughly stirring the solid materials with a long stirring rod; and pouring the solid materials into a liquid material, and using a stirrer to stir at a medium speed for 3 min to 5 min to achieve thorough mixing.

Preferably, the performance index in S8 may be shown in the following table:

| Rating | Evaluation standard |
| --- | --- |
| Prominent | After a temperature is stable, a temperature of the group B remains unchanged. |
| Acceptable | After a temperature is stable, a temperature of the group B is not higher than 18° C. |
| Poor | After a temperature is stable, a temperature of the group B is higher than 18° C. |

Preferably, a specific method for forming the sand and mud layer in S3 may include: sleeving a cement mold outside the equivalent wellbore, adding the sand and mud between the cement mold and the outer cavity body, and compacting with a compactor to simulate the formation; and after the compacting, lifting the cement mold out to form the annular space.

Compared with the prior art, the present disclosure has the following beneficial effects.

1. In the performance evaluation device of a cement for well cementing in a penetrated hydrate layer according to the present disclosure, an outer cavity body is arranged, a partition is arranged in the outer cavity body, and the partition divides a cavity inside the outer cavity body into two independent spaces, namely, an outer circulation cavity and a placement cavity; a low-temperature thermostatic bath is allowed to communicate with the outer circulation cavity through an outer circulation pipeline to form an outer circulation system, which is configured to adjust a temperature of the outer cavity body and simulate a constant temperature state of a formation at infinity; an inner wall of the outer cavity body simulates a formation boundary, which is configured to simulate the stratigraphic geology formed by a cement sheath; an inner cavity body is arranged, an inner circulation cavity is formed inside the inner cavity body, and a high-temperature thermostatic bath is allowed to communicate with an inner circulation cavity through an inner circulation pipeline to form an inner circulation system, which is configured to adjust a temperature of the inner cavity body and simulate a fluid circulation state in an oil pipe; an outer wall of the inner cavity body simulates an outer wall of the oil pipe, which is configured to simulate a wellbore structure formed by the cement sheath; and an equivalent fluid is added to an annular cavity of the equivalent wellbore to simulate the heat conduction of a multi-layer casing pipe. Therefore, the evaluation device of the present disclosure can simulate a true downhole situation and can well meet the research needs.

2. In the performance evaluation device of a cement for well cementing in a penetrated hydrate layer, a stepped hole is formed on the outer cavity body structurally. The formation of the stepped hole facilitates the limit to the equivalent wellbore and facilitates the installation and accurate positioning. In addition, since the stepped hole is through, in the case where the cement sheath and the equivalent wellbore are well consolidated, the stepped hole can be formed to jack up the equivalent wellbore, thereby facilitating the disassembly.

3. The equivalent wellbore of the performance evaluation device of a cement for well cementing in a penetrated hydrate layer has an annular cavity inside, there is a countersunk head screw at two ends of the equivalent wellbore, and after the countersunk head screw is opened, a liquid can be added or discharged, which is convenient for operation.

4. The evaluation device of the present disclosure can conduct an experiment for evaluating the heat insulation performance of a cementing cement; the evaluation device of the present disclosure can conduct experiments at different temperatures, with automatic temperature control; the evaluation device of the present disclosure can automatically eliminate the error of a test system; the evaluation device of the present disclosure can achieve the falling off of a cement sheath mold, such that the device can be recycled; and the evaluation method of the present disclosure can evaluate the heat insulation performance of a cementing cement.

5. The present disclosure innovatively proposes the concept of penetrated hydrate layer and a design method of a cement for well cementing in a penetrated hydrate layer, where deep-water shallow hydrate layers can be classified, and a low-hydration, early-strength, and heat-insulating cement slurry system is adopted for cementing through a penetrated hydrate layer, which provides a new solution to improve the cementing quality of hydrate layers, effectively enriches the theory and technology of cementing engineering, and provides an important guarantee for the safe and efficient exploitation of oil and gas resources in deep-water hydrate layers.

6. The low-hydration, early-strength, and heat-insulating cement slurry system of the present disclosure can effectively isolate a penetrated hydrate layer, ensure the stability of a hydrate during WOC and subsequent production processes, and effectively avoid accidents caused by cementing quality problems.

Figure 1:
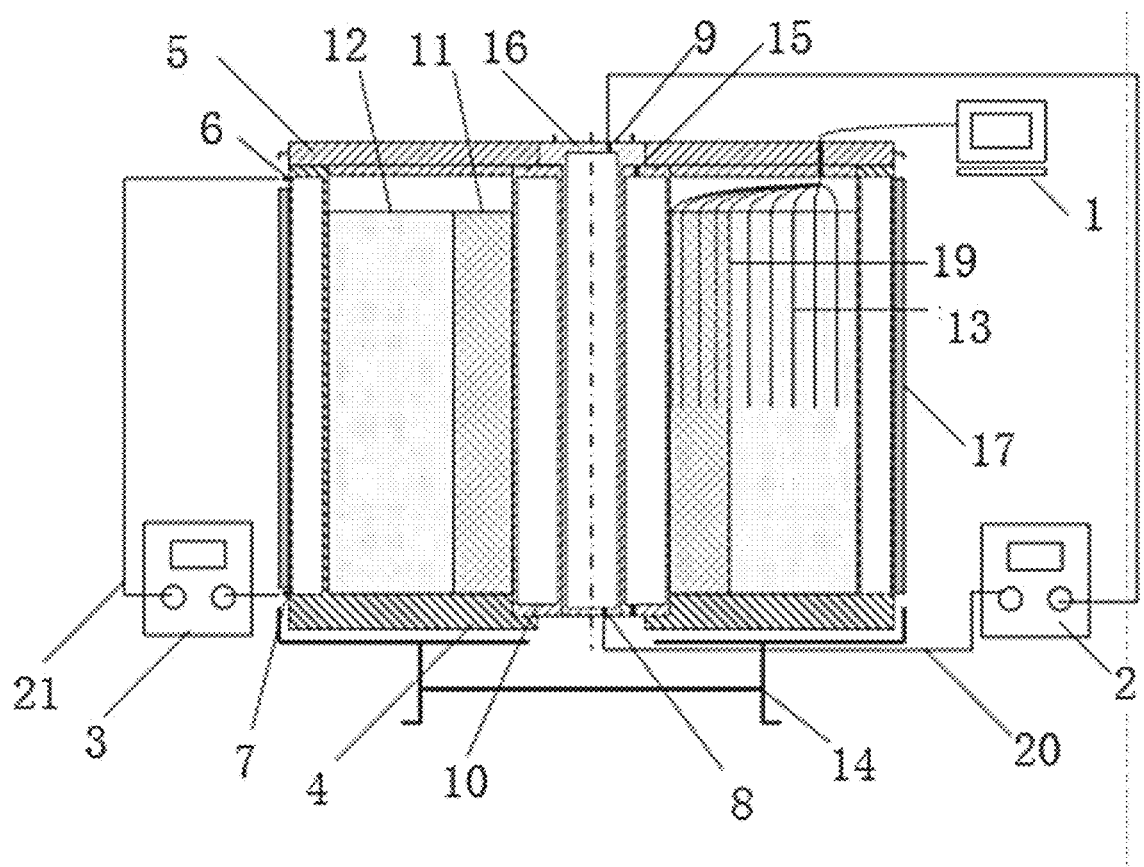
FIG. 1 is a schematic diagram of the overall structure of the present disclosure.

REFERENCE NUMERALS 1 represents a temperature measuring instrument; 2 represents a high-temperature thermostatic bath; 3 represents a low-temperature thermostatic bath; 4 represents an outer cavity, body; 41 represents an outer circulation cavity; 42 represents a placement cavity; 43 represents a stepped hole; 44 represents a partition; 5 represents a thermal insulation cover; 51 represents a central hole; 52 represents a threaded hole; 6 represents an outer-cavity-body water outlet; 7 represents an outer-cavity-body water inlet; 8 represents an inner-cavity-body water inlet; 9 represents an inner-cavity-body water outlet; 10 represents an equivalent wellbore; 101 represents an annular cavity; 102 represents a through-cavity; 11 represents a cement sheath; 12 represents a sand and mud layer; 13 represents a group B of temperature sensors; 14 represents a bracket; 15 represents a countersunk head screw; 16 represents an inner cavity body; 161 represents an inner circulation cavity; 162 represents a capped edge; 17 represents a thermal insulation layer; 18 represents a cement mold; 19 represents a group A of temperature sensors; 20 represents an inner circulation pipeline; 21 represents an outer circulation pipeline; and 22 represents a compactor.

DETAILED DESCRIPTION OF THE EMBODIMENTS

To make the objectives, technical solutions, and advantages of the present disclosure clearer, the present disclosure is further described in detail below with reference to specific implementations. It should be understood that the description is exemplary and is not intended to limit the scope of the present disclosure.

Example 1

Figure 2:
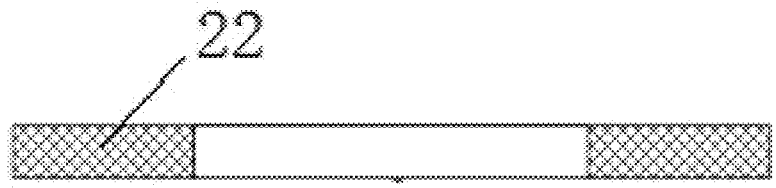
FIG. 2 is a cross-sectional view of a compactor.
Figure 3:
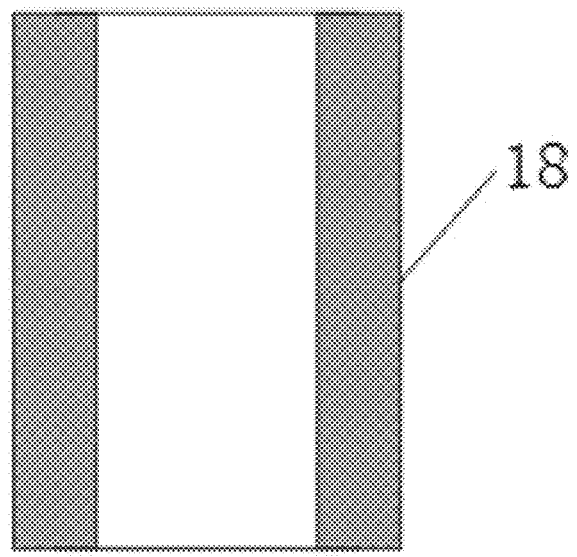
FIG. 3 is a cross-sectional view of a cement mold.
Figure 4:
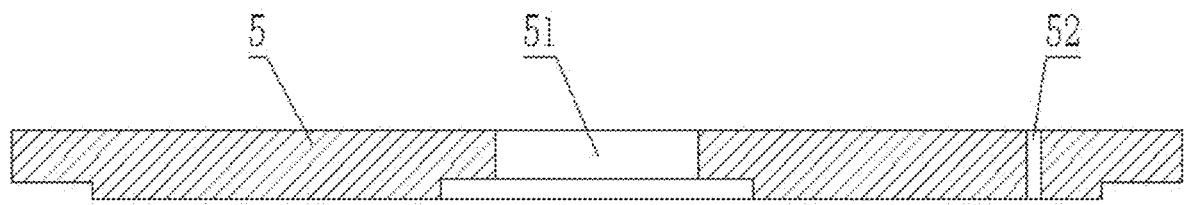
FIG. 4 is a cross-sectional view of a structure of a thermal insulation cover.
Figure 5:
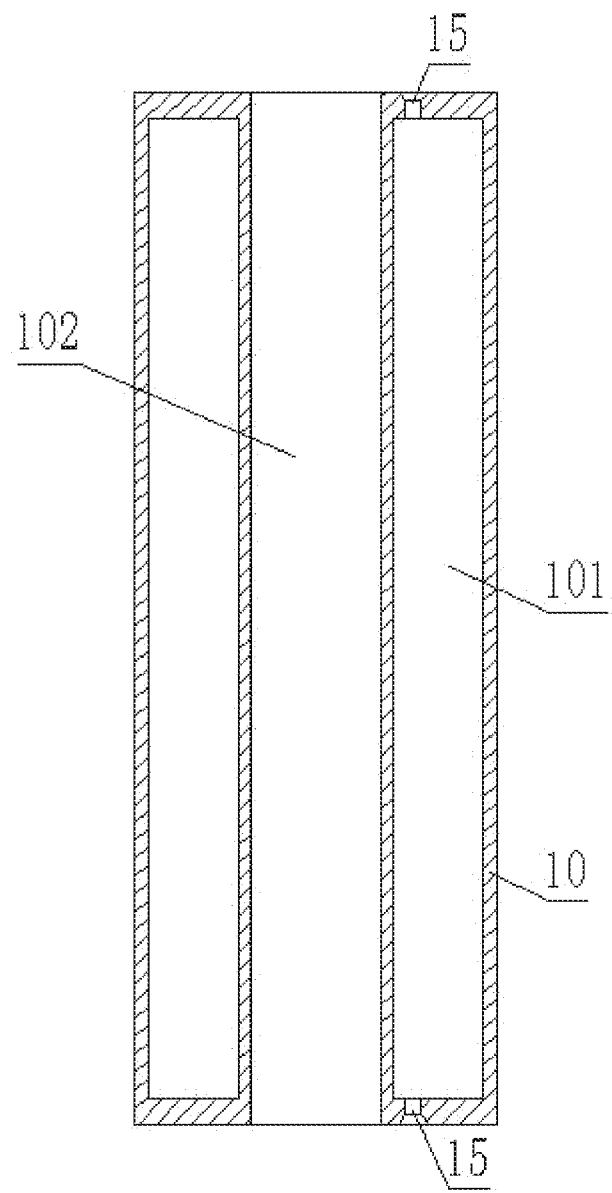
FIG. 5 is a cross-sectional view of a structure of an equivalent wellbore.
Figure 6:
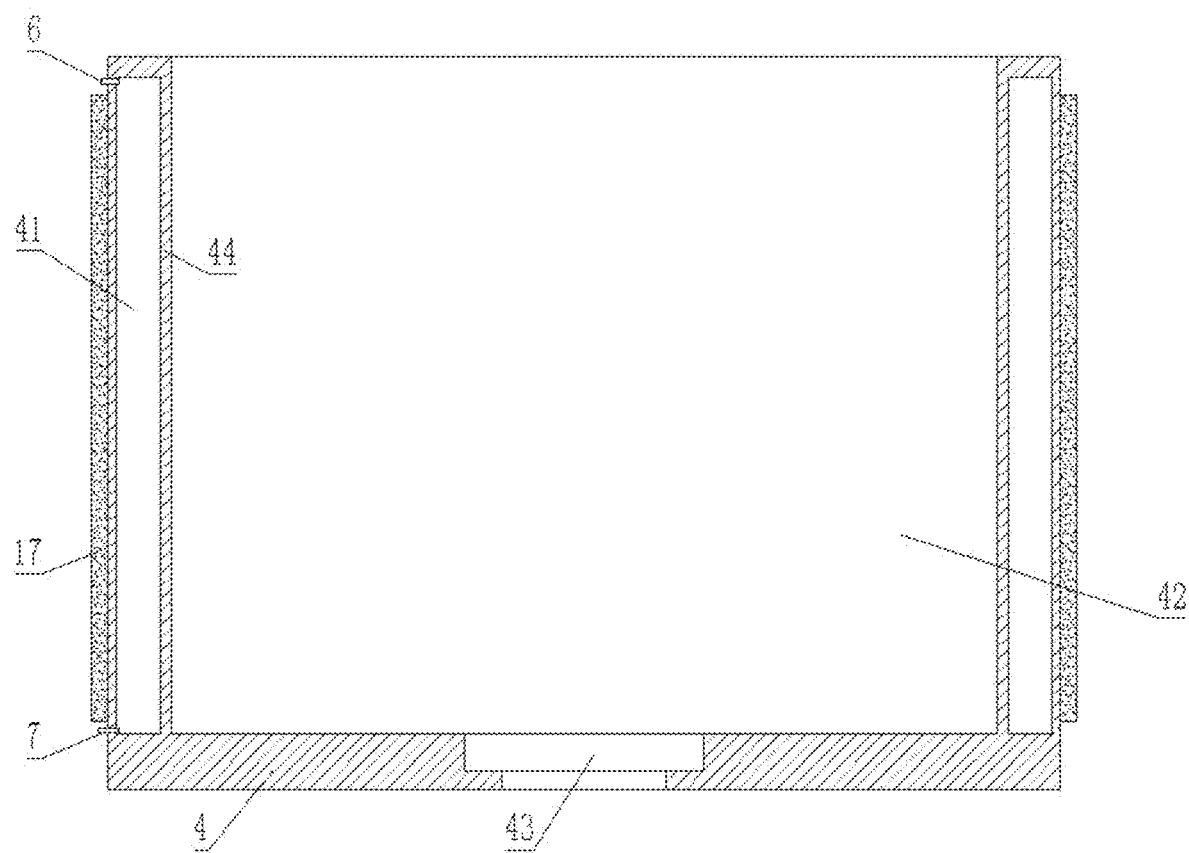
FIG. 6 is a cross-sectional view of a structure of an outer cavity body.
Figure 7:
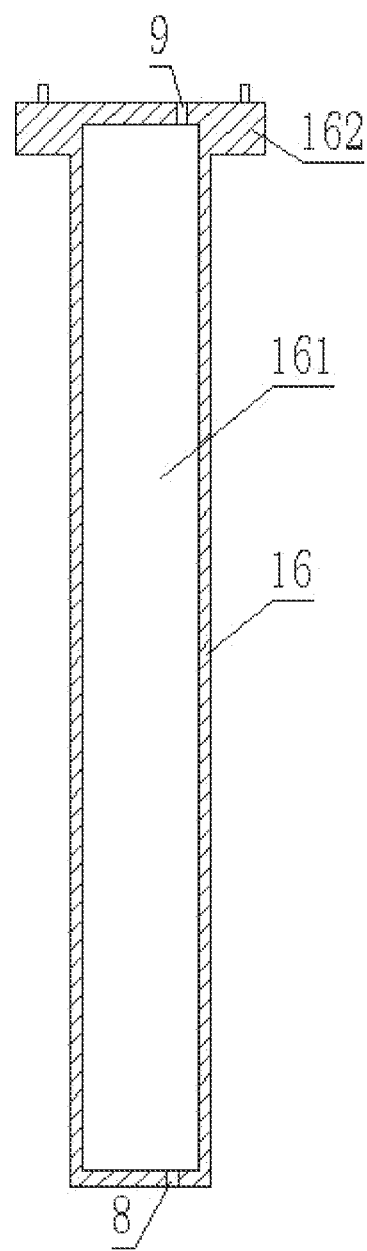
FIG. 7 is a cross-sectional view of a structure of an inner cavity body.
Figure 8:
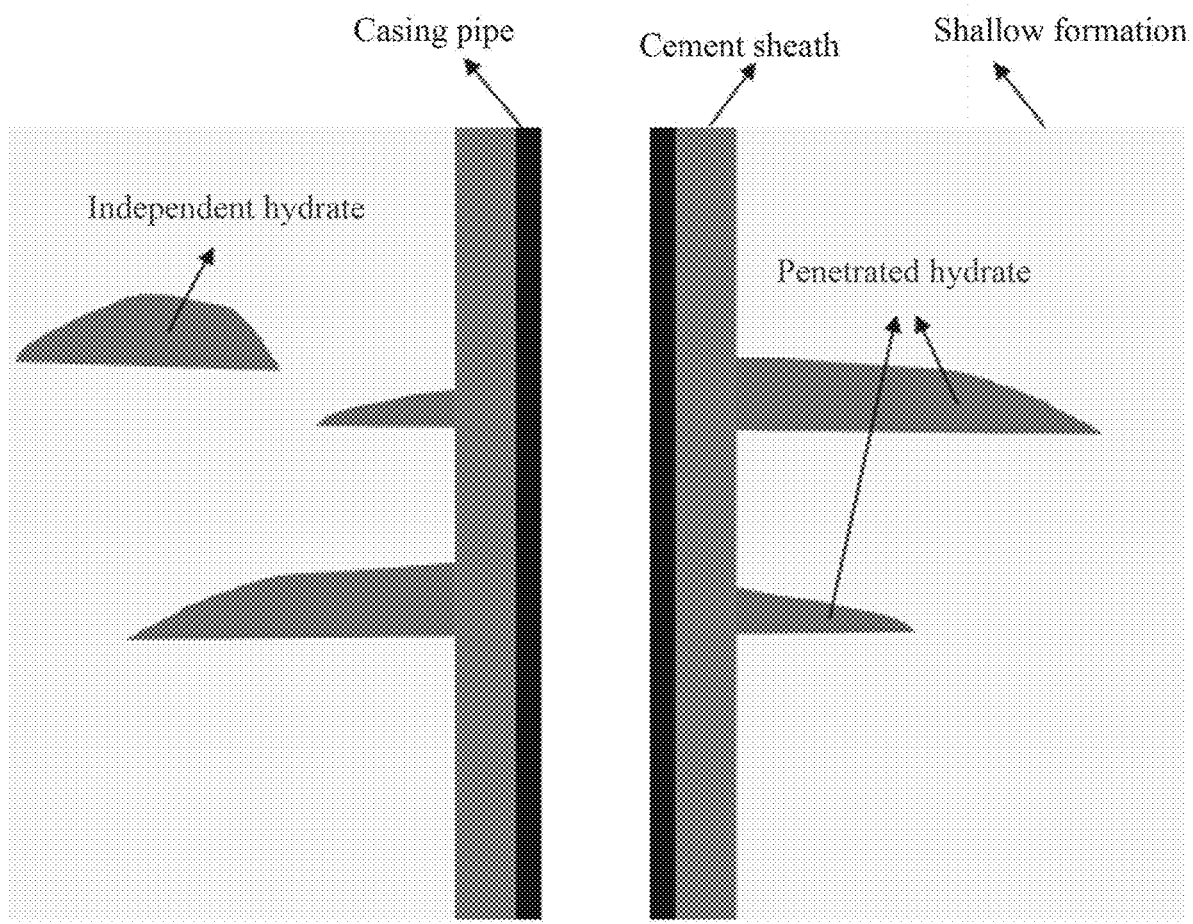
FIG. 8 is a schematic diagram of the penetrated hydrate layer of the present disclosure.

As shown in FIG. 1 to FIG. 7, a performance evaluation device of a cement for well cementing in a penetrated hydrate layer is provided in this example, including:

an outer cavity body 4 with a cavity inside, where a bracket 14 is arranged at a bottom of the outer cavity body 4; a partition 44 is arranged inside the outer cavity body 4, and the partition 44 divides the cavity inside the outer cavity body 4 into two independent spaces, namely, an outer circulation cavity 41 and a placement cavity 42; the outer circulation cavity 41 is a closed cavity body; an outer-cavity-body water inlet 7 and an outer-cavity-body water outlet 6 are formed on the outer circulation cavity 41; and the outer-cavity-body water inlet 7 is arranged at a bottom, and the outer-cavity-body water outlet 6 is arranged at a top, which adopts the structure of water inlet at the bottom and water outlet at the top;

a thermal insulation layer 17 is provided on an outer wall of the outer cavity body 4 to reduce a heat exchange between the cavity body and the external environment; an inner wall of the outer cavity body 4 simulates a formation boundary, which is configured to simulate the stratigraphic geology formed by a cement sheath;

an equivalent wellbore 10 arranged in the placement cavity 42, where a through-cavity 102 that penetrates up and down is formed inside the equivalent wellbore 10, the equivalent wellbore 10 is cylindrical as a whole, and the through-cavity 102 is arranged at a central position of the equivalent wellbore 10 and penetrates up and down; the equivalent wellbore 10 has a double-walled structure, an annular cavity 101 is formed between the two walls, and the annular cavity 101 is a closed cavity for adding an equivalent fluid to simulate the heat conduction of a multi-layer casing pipe; a liquid inlet and a liquid outlet that communicate with the annular cavity 101 are formed at two ends of the equivalent wellbore 10; and a countersunk head screw 15 is threadedly connected in the liquid inlet and the liquid outlet, and a liquid can be added or discharged after the countersunk head screw 15 is opened;

an inner cavity body 16, where the inner cavity body 16 is inserted into the through-cavity 102, and an inner circulation cavity 161 is formed inside the inner cavity body 16; the inner circulation cavity 161 is a closed cavity structure, and an inner-cavity-body water inlet 8 and an inner-cavity-body water outlet 9 are formed at a bottom end and a top end of the inner circulation cavity 161, respectively; a capped edge 162 is arranged at a top of the inner cavity body 16, the capped edge 162 is clamped at the top of the inner cavity body 16, and the capped edge 162 and the inner cavity body 16 can be integrally formed into a T-shape; and two fixed rings are arranged on the top of the inner cavity body 16 for hoisting the inner cavity body 16;

a thermal insulation cover 5 pressed against the outer cavity body 4 and the top of the equivalent wellbore 10, where a central hole 51 is formed on the thermal insulation cover 5, and the capped edge 162 is inserted into the central hole 51; the central hole 51 also has a stepped structure, and the top of the equivalent wellbore 10 can be inserted into the central hole 51; a ring is arranged at an outer side of the thermal insulation cover 5, which is configured to hoist the thermal insulation cover 5; and a threaded hole 52 is also formed on the thermal insulation cover 5;

an outer circulation system including a low-temperature thermostatic bath 3, where the low-temperature thermostatic bath 3 communicates with the outer circulation cavity 41 through an outer circulation pipeline 21 to form an outer circulation system; and the outer circulation pipeline 21 communicates with the outer-cavity-body water inlet 7 and the outer-cavity-body water outlet 6 separately;

an inner circulation system including a high-temperature thermostatic bath 2, where the high-temperature thermostatic bath 2 communicates with the inner circulation cavity 161 through an inner circulation pipeline 20 to form an inner circulation system; and the inner circulation pipeline 20 communicates with the inner-cavity-body water inlet 8 and the inner-cavity-body water outlet 9 separately; and a temperature sensing system, where the temperature sensing system includes a group A of temperature sensors 19, a group B of temperature sensors 13, and a temperature measuring instrument; the group A of temperature sensors 19 and the group B of temperature sensors 13 are arranged in the placement cavity 42 and are each electrically connected to the temperature measuring instrument. The group A of temperature sensors 19 and the group B of temperature sensors 13 are each composed of multiple probes, where removable metal pipes are arranged at an outer side, and temperature sensor probes are arranged at an inner side; and a lower side of the metal pipe is sealed and an upper side of the metal pipe is open, which facilitates the removal from the consolidated cement sheath or formation. In use, the group A of temperature sensors 19 is configured to measure the temperature change of a cement, and the group B of temperature sensors 13 is configured to measure the temperature change of sand and mud. A lead wire of a sensor can be connected to the temperature measuring instrument through the threaded hole 52 reserved on the thermal insulation cover 5.

A stepped hole 43 communicating with the outside is formed at a bottom of the outer cavity body 4, and the equivalent wellbore 10 is fitted in the stepped hole 43. The formation of the stepped hole 43 facilitates the limit to the equivalent wellbore 10 and facilitates the installation and accurate positioning. In addition, since the stepped hole 43 is through, in the case where the cement sheath and the equivalent wellbore 10 are well consolidated, the stepped hole 43 can be formed to jack up the equivalent wellbore 10, thereby facilitating the disassembly.

For the convenience of operation, the performance evaluation device may further include a cement mold 18 for assisting in the filling of sand and mud. The cement mold 18 is configured for assisting in the filling of sand and mud, which has the same size as a required cement sheath 11. The cement mold 18 is arranged annularly, and the cement mold 18 can be sleeved outside the equivalent wellbore 10.

The performance evaluation device may further include a compactor 22 for compacting the sand and mud. The compactor 22 is arranged annularly. The compactor 22 can be sleeved outside the cement mold 18.

In the present disclosure, an outer cavity body 4 is arranged, a partition 44 is arranged in the outer cavity body 4, and the partition 44 divides a cavity inside the outer cavity body 4 into two independent spaces, namely, an outer circulation cavity 41 and a placement cavity 42; a low-temperature thermostatic bath 3 is allowed to communicate with the outer circulation cavity 41 through an outer circulation pipeline 21 to form an outer circulation system, which is configured to adjust a temperature of the outer cavity body 4 and simulate a constant temperature state of a formation at infinity; an inner wall of the outer cavity body 4 simulates a formation boundary, which is configured to simulate the stratigraphic geology formed by a cement sheath; an inner cavity body 16 is arranged, an inner circulation cavity 161 is formed inside the inner cavity body 16, and a high-temperature thermostatic bath 2 is allowed to communicate with an inner circulation cavity 161 through an inner circulation pipeline 20 to form an inner circulation system, which is configured to adjust a temperature of the inner cavity body 16 and simulate a fluid circulation state in an oil pipe; an outer wall of the inner cavity body 16 simulates an outer wall of the oil pipe, which is configured to simulate a wellbore structure formed by the cement sheath; and an equivalent fluid is added to an annular cavity 101 of the equivalent wellbore 10 to simulate the heat conduction of a multi-layer casing pipe. Therefore, the evaluation device of the present disclosure can simulate a true downhole situation and can well meet the research needs.

The evaluation device of the present disclosure can conduct an experiment for evaluating the heat insulation performance of a cementing cement; the evaluation device of the present disclosure can conduct experiments at different temperatures, with automatic temperature control; the evaluation device of the present disclosure can automatically eliminate the error of a test system; and the evaluation device of the present disclosure can achieve the failing off of a cement sheath mold, and such a removable structure enables the device to be recycled.

Example 2

A design method of a cement for well cementing in a penetrated hydrate layer was provided, including be following steps:

(1) A formation sample of a cementing-target penetrated hydrate layer was collected, a temperature and pressure sensor on a drill pipe was used to measure a temperature and a pressure of the formation, and a logging tool was used to measure a hydrate saturation.

(2) The obtained physical parameters of the formation were analyzed, early strength performance requirements of a cement slurry that meets cementing conditions were determined based on field operation requirements, and hydration heat limits and heat insulation performance limits of the cement slurry were determined based on formation temperature and pressure conditions, temperature and pressure curves of hydrate decomposition, and thermodynamical equations.

(3) According to the early strength performance requirements of the cement slurry, effects of various early-strength agents were tested until an early-strength agent with the optimal performance was determined.

(4) According to the hydration heat performance requirements of the cement slurry, effects of various low-hydration-heat materials were tested until a low-hydration-heat material with the optimal performance was determined.

(5) According to the heat insulation performance requirements of the cement slurry, effects of various heat-insulating materials were tested until a heat-insulating material with the optimal performance was determined. The heat-insulating material includes, but is not limited to, an HUM, obturator perlite, or a VMB.

(6) The optimal early-strength agent, low-hydration-heat material, and heat-insulating material and the cement slurry were prepared into the low-hydration, early-strength, and heat-insulating cement slurry system to adjust the performance of the cement slurry, such that the cement slurry had low hydration, early strength, and heat insulation performance and met the requirements of cementing construction.

(7) The performance evaluation device of a cement for well cementing in a penetrated hydrate layer described in Example 1 was used to simulate the entire process of cement slurry pumping and solidification in a hydrate formation environment. A core of a target layer after 24 hours was extracted and tested for compressive strength, and a solidification strength of the cement slurry under true construction conditions was predicted; the stability detection module was used to detect whether the hydrate is decomposed during a solidification stage of the cement slurry; and the production simulation module was used to simulate whether the hydrate is decomposed during a production process to test whether the performance of the low-hydration, early-strength, and heat-insulating cement slurry system meets the requirements.

(8) A cement slurry injection volume required by the target layer was estimated, and the optimized low-hydration, early-strength, and heat-insulating cement slurry was injected into the formation in the form of a displacement liquid according to field operation conditions and corresponding construction parameters until the cement slurry reached a predetermined solidification range. The cement sheath formed after the cement slurry is solidified has prominent early strength, which ensures the cementing quality. Moreover, the low-hydration-heat material and the heat-insulating material existing inside can ensure the stability of a hydrate during WOC and subsequent production processes, which effectively avoids accidents caused by hydrate instability.

The determining whether the performance of the low-hydration, early-strength, and heat-insulating cement slurry system meets the requirements in step (7) may include the following specific steps:

S1: An equivalent wellbore 10 was placed into the placement cavity 42 inside the outer cavity body 4, and an equivalent fluid was added to an annular cavity 101 of the equivalent wellbore 10.

Specifically, the countersunk head screw 15 at the upper side was unscrewed, an equivalent fluid was added, and then the countersunk head screw 15 was tightened.

A thermal conductivity coefficient of the equivalent fluid was calculated according to the following formula:

$$R = \sum \frac{1}{\lambda_i} \ln \frac{r_{i+1}}{r_i}$$

where R represents a thermal resistance; $\lambda$ represents a thermal conductivity coefficient, W/(m*k); and r represents a radius, m.

S2: The inner cavity body 16 was hoisted into the through-cavity 102 of the equivalent wellbore 10, and lowered until the capped edge 162 at an upper end of the inner cavity body 16 was clamped at the upper end of the equivalent wellbore 10; and the high-temperature thermostatic bath 2 was allowed to communicate with the inner circulation cavity 161 through the inner circulation pipeline 20 to form an inner circulation system.

S3: Sand and mud was added into the placement cavity 42 inside the outer cavity body 4 to form an annular sand and mud layer 12, the sand and mud layer was compacted, and an annular space was reserved between the sand and mud layer 12 and an outer wall of the equivalent wellbore.

S4: The prepared cement slurry was slowly poured into the annular space between the sand and mud layer and the outer wall of the equivalent wellbore; and when the cement was slightly solidified, metal shells of the group A of temperature sensors 19 were inserted into the cement at equal intervals in a radial direction, and metal shells of the group B of temperature sensors 13 were inserted into the sand and mud at equal intervals in the radial direction, where the metal shells were inserted at a depth that makes a bottom end of the metal shell in the middle of the cement or the sand and mud.

S5: After the cement was completely solidified, probes of the group A and group B of temperature sensors 13 were inserted into the metal shells sequentially, and the probes were allowed to pass through the thermal insulation cover 5 and connected to the temperature measuring instrument.

S6: The low-temperature thermostatic bath 3 was allowed to communicate with the outer circulation cavity 41 through the outer circulation pipeline 21 to form an outer circulation system, the low-temperature thermostatic bath 3 was opened and the thermal insulation cover 5 was covered to cool the entire device, and the experiment was started after a temperature was stable.

S7: The high-temperature thermostatic bath 2 was opened to heat the inner cavity body 16, a temperature change curve of each temperature sensor was recorded, and the high-temperature thermostatic bath 2 and the low-temperature thermostatic bath 3 were closed when a temperature remained unchanged; and the sensors were taken out, and then the rest components were taken out sequentially.

S8: An experimental result was compared with a performance index, and a heat insulation performance rate of the cement slurry used in the experiment was determined to evaluate the performance of the cement.

A preparation method of the cement slurry in S4 may be as follows: according to a required cement sheath cementing experiment, various solid materials (cement dry ash, density-reducing agent, and solid components in various additives) are weighed by an electronic scale based on a cement slurry formula given on site, poured into a bucket, and thoroughly stirred with a long stirring rod; and the solid materials are poured into a liquid material such as tap water and a defoaming agent, and a stirrer is used to stir at a medium speed for 3 min to 5 min to achieve thorough mixing. The prepared cement slurry can be slowly poured into the cement sheath annular space.

Specifically, the performance index in S8 may be shown in the following table:

| Rating | Evaluation standard |
| --- | --- |
| Prominent | After a temperature is stable, a temperature of the group B remains unchanged. |
| Acceptable | After a temperature is stable, a temperature of the group B is not higher than 18° C. |
| Poor | After a temperature is stable, a temperature of the group B is higher than 18° C. |

Specifically, a specific method for forming the sand and mud layer in S3 may be as follows: a cement mold 18 is sleeved outside the equivalent wellbore 10, the sand and mud is added between the cement mold 18 and the outer cavity body 4 and compacted with a compactor 22 to simulate the formation; and after the compacting, the cement mold 18 is lifted out to form the annular space. The annular space is provided to form a cement sheath 11.

What is claimed is:

1. A performance evaluation device of a cement for well cementing in a penetrated hydrate layer, comprising:
an outer cavity body with a cavity inside, wherein a partition is arranged inside the outer cavity body, and the partition divides the cavity inside the outer cavity body into an outer circulation cavity and a placement cavity; and a thermal insulation layer is arranged on an outer wall of the outer cavity body;
an equivalent wellbore arranged in the placement cavity, wherein a through-cavity penetrating up and down is formed inside the equivalent wellbore; the equivalent wellbore has a double-walled structure, and an annular cavity is formed between two walls of the equivalent wellbore; and a liquid inlet and a liquid outlet each communicating with the annular cavity are formed at two ends of the equivalent wellbore, respectively;
an inner cavity body inserted into the through-cavity, wherein an inner circulation cavity is formed inside the inner cavity body; and a capped edge is arranged at a top of the inner cavity body, and the capped edge is clamped at the top of the inner cavity body;
a thermal insulation cover pressed against the outer cavity body and a top of the equivalent wellbore;
an outer circulation system comprising a low-temperature thermostatic bath, wherein the low-temperature thermostatic bath communicates with the outer circulation cavity through an outer circulation pipeline to form the outer circulation system;
an inner circulation system comprising a high-temperature thermostatic bath, wherein the high-temperature thermostatic bath communicates with the inner circulation cavity through an inner circulation pipeline to form the inner circulation system; and a temperature sensing system, wherein the temperature sensing system comprises a first group of temperature sensors, a second group of temperature sensors, and a temperature measuring instrument, and the first group of temperature sensors and the second group of temperature sensors are arranged in the placement cavity and are each electrically connected to the temperature measuring instrument.

2. The performance evaluation device of the cement for well cementing in the penetrated hydrate layer according to claim 1, wherein a stepped hole communicating with an outside is formed at a bottom of the outer cavity body, and the equivalent wellbore is fitted in the stepped hole.

3. The performance evaluation device of the cement for well cementing in the penetrated hydrate layer according to claim 1, wherein a countersunk head screw is threadedly connected in the liquid inlet and the liquid outlet, respectively.

4. The performance evaluation device of the cement for well cementing in the penetrated hydrate layer according to claim 1, wherein a central hole is formed on the thermal insulation cover, and the capped edge is inserted into the central hole.

5. The performance evaluation device of the cement for well cementing in the penetrated hydrate layer according to claim 1, further comprising a cement mold for assisting in a filling of sand and mud.

6. The performance evaluation device of the cement for well cementing in the penetrated hydrate layer according to claim 1, further comprising a compactor for compacting sand and mud.

7. The performance evaluation device of the cement for well cementing in the penetrated hydrate layer according to claim 1, wherein performance evaluated by the performance evaluation device is physicochemical thermal performance of the cement, comprising cement hydration exothermic performance, cement paste strength performance, and cement paste thermal conductivity.

* * * * *